United States Patent [19]

Sedon

[11] 4,360,698
[45] Nov. 23, 1982

[54] PROCESS FOR MAKING GLYCOL ETHERS UTILIZING A HETEROGENEOUS CATALYST

[75] Inventor: James H. Sedon, Midland, Mich.

[73] Assignee: The Dow Chemical Company, Midland, Mich.

[21] Appl. No.: 286,093

[22] Filed: Jul. 22, 1981

[51] Int. Cl.$^3$ ............................................. C07C 41/03
[52] U.S. Cl. ................................... 568/618; 568/606; 568/607; 568/611; 568/614; 568/616; 568/620; 568/659; 568/660; 568/661; 568/662; 568/663; 568/664; 568/670; 568/673; 568/675; 568/676; 568/678; 568/679; 568/680
[58] Field of Search ............... 568/606, 607, 611, 618, 568/620, 616, 614, 659–664, 670, 673, 675–676, 678–680

[56] References Cited

U.S. PATENT DOCUMENTS

| | | | |
|---|---|---|---|
| 3,954,884 | 5/1976 | Kedwell | 568/620 |
| 4,278,820 | 7/1981 | Kametaka et al. | 568/618 |
| 4,282,387 | 8/1981 | Olstowski et al. | 568/618 |

FOREIGN PATENT DOCUMENTS

| | | | |
|---|---|---|---|
| 6105 | 1/1980 | European Pat. Off. | |
| 2917085 | 11/1979 | Fed. Rep. of Germany | 568/678 |
| 38-4858 | 4/1963 | Japan | 568/678 |
| 49-24449 | 6/1974 | Japan | 568/618 |
| 676891 | 8/1952 | United Kingdom | 568/618 |

OTHER PUBLICATIONS

Shih Yu, "Manufacture of Ethylene Glycol Derivatives as De-Icing Agent for Aviation Gasoline," 93 Chemical Abstracts 10461k (1980).
Morrison and Boyd, Organic Chemistry, 3rd Ed., (1973) p. 564.
Nippon Shokubai Kagaku, Alkylene Glycol Ether Production Catalyst etc., Derwent 06465D.
Kametaka, "Ethylene Glycol Monoethyl Ether," 93 Chem. Abstracts 220375m (1980).
Weibull, "Reaction Product of an Organic Compound Containing a Reactive Hydrogen and an Epoxide," 86 Chemical Abstracts 172162w (1977).

Primary Examiner—Howard T. Mars
Attorney, Agent, or Firm—Douglas N. Deline; Cedric M. Richeson

[57] ABSTRACT

A process to form glycol ethers by reacting an organic compound (A) having at least one aliphatic hydroxyl group with an oxirane compound (B) under reaction conditions in the presence of a catalytic amount of a polymeric material that is substantially insoluble in the reaction mixture, said polymeric material having a plurality of pendant sulfonate moieties with divalent metal counterions. Preferential formation of the mono adduct of glycol ethers is noted.

19 Claims, No Drawings

PROCESS FOR MAKING GLYCOL ETHERS UTILIZING A HETEROGENEOUS CATALYST

BACKGROUND OF THE INVENTION

The present invention relates to processes for the production of glycol ethers and more particularly to the catalyzed production of glycol ethers.

It is known to react organic compounds having at least one aliphatic hydroxyl group with oxirane compounds to obtain glycol ethers. Aspects of these known processes are shown in U.S. Pat. Nos. 2,684,387; 3,972,948 and 3,935,279. A range of reactants, catalysts and reactant conditions are shown to produce products having many utilities, for example, as components of brake fluids, cleaning fluids, solvents for dyes, paints, and lacquers and as chemical intermediates. In particular the mono adduct (n=1) of glycol ethers having the formula

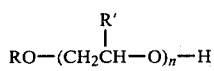

wherein R is an organic group, R' is hydrogen or an organic group and n is a positive integer, is a preferentially valued product relative to the higher adducts (n≧2) under certain market conditions. Enhancement of the mono adduct (n=1) component in the product mixture resulting from the reaction of oxirane compounds with hydroxyl group containing compounds can be economically advantageous. Correspondingly, limiting the production of the higher adducts (n≧2), commonly called highers, as well as limiting formation of glycols, polymers and by-products is often deemed desirable. Achieving this selectivity with reduced recycling, reprocessing and/or separation costs is particularly desirable. Therefore, process parameters including catalysts that may be successfully incorporated into a process to economically provide a degree of selectivity and control over the resultant product mix are much sought after in the industry.

Many catalysts have been used in the reaction of an oxirane compound with compounds having hydroxyl groups. Each has its own relative advantages and disadvantages. Acid catalyzed and base catalyzed reactions both yield hydroxyethers; see e.g. Morrison and Boyd, *Organic Chemistry*, 3rd Ed., (1973), p. 564. Acid catalysts allow production at lower temperatures than bases, but form undesirable byproducts; see e.g. U.S. Pat. No. 3,954,884 which describes the use of sulfuric acid, toluene sulfonic acid, sulfonated polystyrene and sulfonated styrene-divinylbenzene copolymers among others as catalysts. Alkali metal and alkaline earth metal hydroxide bases have been commonly used as catalysts in the reaction, in addition to those patents mentioned above, see, for example, European Patent Application No. 6105. These catalysts require removal or neutralization before purification of the product. The typical base catalysts NaOH and KOH introduce water into the reaction mixture from alkoxide formation. This results in consequential glycol impurities. Also both strong acid and strong base catalysts tend to be corrosive. The catalyst removal techniques employed, e.g. distillation, acid neutralization with distillation and/or filtration all result in additional energy requirements, yield losses or large waste streams. Thus, prior art catalysts have had problems achieving the goals of noncorrosivity, low by-product formations, ease of separation and catalytic effectiveness.

A heterogeneous catalyst obviates some of the above-mentioned problems associated with separating the catalyst from the reaction mixture. Such catalysts which are insoluble in the reaction mixture have been sought and polymeric materials have been used as such with varying degrees of success; see, e.g. U.S. Pat. No. 4,011,268 which describes the use of polymeric materials having tetraalkyl phosphonium alkoxide, aryloxide or hydroxide containing pendant groups. These catalysts have disadvantages including early deterioration at reaction temperatures and high catalyst cost.

Other catalysts that have been employed such as those described in U.S. Pat. Nos. 1,774,089; 1,882,564; 2,327,053; 2,527,970; 2,807,651; and 3,354,227 which describe, among others, as catalysts sulfates of polyand divalent metals; dialkyl sulfates; zinc, nickel and chromium sulfates; metal, alkali metal and alkaline earth metal salts; metal chlorides and sulfur dioxide. These catalysts suffer from several disadvantages including formation of undesirable amounts of impurity products such as dioxane, aldehydes and polymers and too high solubilities which make these catalysts difficult to remove from the reaction mixture. Further disadvantages of some of these catalysts include slow reaction rates and excessive toxicity and corrosivity.

Heretofore, a catalyst that is substantially insoluble in the reaction mixture (heterogeneous) has not been described which also allows the particular process advantages hereinafter described.

SUMMARY OF THE INVENTION

It is an object of this invention to provide a process for the manufacture of glycol ethers wherein the reaction is catalyzed utilizing a catalyst which avoids or substantially reduces disadvantages of the prior art.

A further object of this invention is to provide a process employing a catalyst which is easily separable from the product mixture.

A further object of this invention is to provide a process employing a catalyst which may be used to produce higher yields of the desired products.

A further object of this invention is to provide a process which may be operated at lower temperatures to effect energy and cost savings.

A further object of this invention is to provide a process which reduces byproducts, waste streams, and recycling cost.

A further object of this invention is to provide a process which allows flexibility in operation as to process reaction conditions and product mixtures.

A further object of this invention is to provide a less corrosive catalyst.

The foregoing objects and others which will become apparent from that which follows are achieved in a process which reacts an organic compound having at least one aliphatic hydroxyl group with an oxirane compound to form a glycol ether. It is not necessary that each and every object listed above be found in all embodiments of the invention. It is sufficient that the invention may be advantageously employed when compared to the prior art. Fundamental to the invention is the use of a polymeric material having pendant salt moieties with divalent metal counterions to catalyze the reaction. This polymeric material should be insoluble in the reaction mixture and preferably resistant to degradation so that the product mixture may be readily separated therefrom. Use of this polymeric material as a catalyst has as a feature the ability to promote preferentially the production of the mono adduct of the glycol ether products. Advantageously, the temperature of the reaction mixture may often be reduced from that utilized in prior art processes to yield an equivalent or superior product mix. Also the catalyst generally being in a salt rather than acid or base form tends to be less corrosive than the corresponding non-salt forms.

DETAILED DESCRIPTION OF REPRESENTATIVE EMBODIMENTS

As mentioned above, the invention employs as a reactant an organic compound (A) which has at least one aliphatic hydroxyl group. Any compound which contains an aliphatic hydroxyl group, i.e., a hydroxyl group not directly attached to an aromatic ring, may be reacted with an oxirane compound (B) according to the process of this invention, but it is preferable to use one which contains no other groups that are reactive with the oxirane group. Such a compound may be a monohydric, dihydric, trihydric or polyhydric alcohol. The alcohols may be primary, secondary or tertiary in character and may be saturated or unsaturated as well as substituted with various substituents.

Examples of various monohydric alcohols include such alcohols as methyl, ethyl, n-propyl, isopropyl, n-butyl, isobutyl, sec-butyl, t-butyl, pentyl, heptyl, decyl, cyclopentanol, allyl, crotyl, methylvinyl carbinol, benzyl, β-phenylethyl and cinnamyl. Preferred are those containing less than 12 carbon atoms with the compounds methanol, ethanol and n-butanol being especially preferred.

Dihydric and polyhydric alcohols may also be used such as ethylene glycol, propylene glycol, glycerol, as well as sugars such as mannitol, sorbitol, etc.

Less preferred hydroxy compounds are those which contain in addition to hydroxy groups, such groups as amino groups, carboxyl groups, carboxylic acid groups, etc., which are also reactive with the oxirane compound in competition with the hydroxy group.

The invention also employs as a reactant an oxirane compound (B). Such a compound contains at least one oxirane group and is of the formula

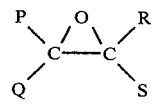

wherein P, Q, R and S are substituent groups. Such oxirane groups may be either internally or terminally located. If terminally located, then one or both of the groups P, Q and R, S are elemental groups, e.g., a hydrogen or chlorine atom. For example, ethylene oxide is a suitable oxirane compound having two terminal oxirane groups with both group P, Q and group R, S consisting of attached elemental groups viz. hydrogen groups. Additional examples of oxirane compounds having terminally located oxirane groups are propylene oxide and butylene oxide.

Suitable oxirane compounds may include as substituents on P, Q, R or S such nonlimiting examples as alkyl, aryl, alkaryl, aralkyl, cycloparaffinic, naphthyl, anthryl, phenanthryl, acenaphthenyl, naphthacyl, chrysyl, pyryl, benzohydryl, terphenylyl, methyl, ethyl, propyl, isopropyl, butyl, isobutyl, t-butyl, amyl, isoamyl, hexyl, isohexyl, heptyl, octyl, nonyl, decyl, undecyl, dodecyl, tridecyl, tetradecyl, pentadecyl, hexadecyl, heptadecyl, octadecyl, nonadecyl, eicosyl, phenyl, tolyl, ethylphenyl, propylphenyl, cyclopentyl, cyclohexyl, benzyl, biphenyl, camphanyl, cinnamyl, cuminyl, cumyl, cymyl, duryl, fenchanyl, phenethyl, phenpropyl and phenbutyl, including halosubstituted derivatives thereof as further illustrated by the following specific examples. The hydrocarbon substituent groups P, Q, R and S may contain from 1 to 25 carbon atoms, and preferably 1 to 5 carbon atoms. Species of organic epoxides, which are oxirane compounds having the ring oxygen atom attached to two adjacent carbon atoms, include ethylene oxide, propylene oxide, 1,2-butylene oxide, 2,3-butylene oxide, 1,2-pentene oxide, 2,3-pentene oxide, 1,2-hexene oxide, 2,3-hexene oxide, 3,4-hexane oxide, 1,2-heptene oxide, 2,3-heptene oxide, 3,4-heptene oxide, 1,2-octene oxide, 2,3-octene oxide, 3,4-octene oxide, 1,2-nonene oxide, 2,3-nonene oxide, 3,4-nonene oxide, 4,5-nonene oxide, 1,2-decene oxide, 2,3-decene oxide, 3,4-decene oxide, 1,2-dodecene oxide, phenyl ethylene oxide, 3-phenyl-1,2-propylene oxide, naphthyl ethylene oxide, 1-methylphenyl ethylene oxide, 3-cyclohexyl propylene oxide, 3-chlorophenyl ethylene oxide, 3-phenethyl-1,2-butylene oxide, 4-tolyl-1,2-butylene oxide, 5-cuminyl-1,2-pentene oxide, 1,2-dibutyl ethylene oxide, 1,2-diamyl ethylene oxide, 1,2,3-trimethyl ethylene oxide, 1,2,3,4-tetramethyl ethylene oxide, α-epichlorohydrin and epibromohydrin.

The preferred oxirane compounds are ethylene oxide, propylene oxide and 1,2-butylene oxide.

The invention also employs as a catalyst a polymeric material having a plurality of pendant sulfonate moieties with divalent metal counterions. The pendant sulfonate moieties are anions which are chemically associated with charge balancing divalent metal cations. These divalent metal cations are preferably cations of those elements found in Groups 2a, 2b and 8 of a typical modern Mendeleefian Periodic Table of the Elements. An example of such table is found on the inside cover of the 58th Edition of the CRC Handbook of Chemistry and Physics (1977–1978) published by CRC Press, Inc. Examples of these divalent metal cations include magnesium, calcium, zinc and iron. The alkaline earth metal cations (Group 2a) and the Fe++ cation are to be preferred and the magnesium cation is particularly advantageous.

Examples of such polymeric material include sulfonated styrene-divinylbenzene copolymers whose ionic form contains divalent metal cations. Copolymers of this type are resins whose ratio of styrene to divinylbenzene may vary from about 100:1 to about 7:1. These resins are manufactured by many techniques and sold under a variety of tradenames. One example of such a copolymer resin is Dowex ® MSC-1 (trademark of The Dow Chemical Company) brand copolymer resin which is manufactured by The Dow Chemical Company of Midland, Mich. Dowex ® MSC-1 cation exchange resin is a sulfonated, macroporous, highly crosslinked styrene-divinylbenzene copolymer. Reference is made to U.S. Pat. No. 3,549,562 as teaching a typical process for manufacture of suitable resins and that teaching is hereby incorporated. Another example is the macroporous ion-exchange resin sold by the Rohm and Haas Company of Philadelphia, Pa. under the tradename Amberlyst 15.

Other sulfonated resins may be used; illustrative are resins such as sulfonated polyethylene beads, or perfluorosulfonic acid polymeric materials such as that manufactured under the trademark Nafion ® by E. I. DuPont de Nemours & Company. Typically, resins are manufactured in hydrogen form, but may be converted from hydrogen or other ionic forms to those forms of the invention desired (see above) by conventional ion exchange techniques already known to those skilled in the art. The amount of resin converted can be varied. The optimum degree of exchange for a particular process of the invention as well as optimization of other process parameters is within the skill of the art and deemed an obvious modification of the invention. It is generally believed that the typical preferred catalysts are over 90 percent exchanged.

The aforementioned polymeric materials of the invention are substantially insoluble in the reaction mixture. By substantially insoluble is meant that the polymeric material is typically less soluble than the corresponding nonpolymer-bound metal counterion salts, e.g., when the metal counterion is $Mg^{++}$, the Mg form of the catalyst should be less soluble in the reaction mixture than $MgSO_4$. Generally, this means that the effluent from the reaction vessel of the process of the invention should have less than 55 parts per million of dissolved metal counterion present and preferably less than 1 part per million. When the process achieves the preferred state of having less than 1 part per million of dissolved metal counterion in the effluent, then the polymeric material is termed to be "essentially insoluble".

It is to be noted that the reaction may be advantageously carried out in batch, semi-batch, or continuous reactors with either a slurry or packed bed of the aforementioned catalysts.

The temperature at which the reaction may be carried out may be in a range of from about 40° C. to about 180° C. or higher. The operational temperature will depend upon the particular catalyst used as well as the particular reactants. Temperatures of about 180° C. and higher will cause some resins which may be embodied in the process to decompose. Conversely, temperatures approaching and exceeding a lower limit of 40° C. produce a much slower rate of reaction. It is to be further noted that the process may be run preferentially at a temperature from about 80° C. to about 120° C. This temperature range is typically less than that preferentially found in similar reactions which utilize bse catalysts such as NaOH or KOH.

The pressure may vary from about 20 psig to about 1000 psig. The representative preferred embodiments of the invention were all conducted under autogenous (self-generated) pressure.

The reaction time may also vary from about 1 to about 600 minutes or higher depending upon other reaction conditions. It has been found that while the reaction should be carried out for a sufficient time to allow formation of products if the reaction is allowed to continue too long the production of highers and by-products is enhanced. It is preferred to allow the reaction to occur from about 30 minutes to about 120 minutes.

Also, the molar ratios of reactants may vary such that the ratio of Compound A to Compound B is from about 100:1 to about 1:2, but preferably from about 8:1 to about 1:2. The most preferred ratio for obtaining the mono adduct is about 3:1.

A catalytic amount of sulfonated polymeric material having divalent metal counterions is required for the practice of this invention. Typically, the aforementioned polymeric material is present in a minimum weight ratio of polymeric material:combined reagents of about 1:50 and preferably of about 1:4. A maximum polymeric material:combined reagents weight ratio is typically of about 2:1 and preferably of about 1:2. These maximum and minimum ratios are only typical with the actual ratios determined by practical considerations, such as convenience and economy. Also, it is important to note that the above ratios designate a range and that the preferred amount of catalyst will vary depending upon the particular process parameters chosen.

Therefore, the most preferred conditions for the invention would be reacting $C_1$-$C_4$ monohydric aliphatic alcohols with ethylene oxide utilizing from about 5 to about 50 weight percent of a magnesium exchanged sulfonated styrene-divinylbenzene copolymer catalyst at 80° C.–120° C., at autogenous pressure, for 0.5–2.0 hours, with an alcohol:oxide molar ratio of 3:1.

The following examples are given to illustrate the advantages of the invention, but should not be construed as limiting the scope.

EXAMPLE 1

$Mg^{++}$ form Dowex ® MSC-1 Catalyst

A bed of the $Mg^{++}$ form of Dowex ® MSC-1 resin was prepared by the following procedure: 60 g of the $H^+$ form of the resin was placed in a 116 ml stainless steel tube reactor and was washed with 20 bed volumes of 5 percent aqueous $MgCl_2$ solution followed by 40 bed volumes of distilled water. A bed volume is the available volume of the reactor subsequent to its being loaded with catalyst.

The bed was drained and then washed with 40 bed volumes of anhydrous ethanol. A mixture of 25 weight percent ethylene oxide and 75 weight percent ethanol was fed through the bed whose temperature was controlled at 102° C. The flow rate was such that the residence time was 60 minutes.

The effluent from the reactor was analyzed by standard gas chromatographic techniques. The effluent contained 39.9 weight percent ethylene glycol monoethyl ether (EE), 4.7 weight percent diethylene glycol monoethyl ether (DE) and 0.9 weight percent of triethylene glycol monoethyl ether (TE). The ratio of the mono adduct (EE) to highers (DE and TE and polyadducts) was 7.8:1.0 on a weight basis.

EXAMPLE 2

$Fe^{++}$ form Dowex ® MSC-1 Catalyst

The reaction of Example 1 was carried out with the same feed mixture and conditions except the catalyst utilized was prepared by washing the $H^+$ form of the resin with a 10 percent $FeSO_4$ solution instead of 5 percent $MgCl_2$. This reaction yielded a product containing 32.4 weight percent EE, 2.7 weight percent DE and 0.3 weight percent TE. The ratio of the mono adduct (EE) to highers was 10.8:1.0.

EXAMPLE 3

KOH Catalyst (Not of the Invention)

The reaction of Example 1 was carried out with the same feed mixture and conditions except utilizing 0.02 g KOH per 100 g feed as the catalyst at 150° C. for 2 hours. This reaction yielded a product containing 27.1 weight percent EE, 9.7 weight percent DE and 0.9 weight percent TE. The ratio of the mono adduct (EE) to the highers was 2.6:1.0.

EXAMPLE 4

$Mg^{++}$ form Dowex® MSC-1 Catalyst

The catalyst of Example 1 was washed with 60 bed volumes of n-butanol. A mixture of 14.9 weight percent ethylene oxide and 85.1 weight percent n-butanol were pumped through the bed whose temperature was controlled at 100° C. with a residence time of 60 minutes.

The effluent yielded a product containing 29.0 weight percent ethylene glycol mono n-butyl ether (EB), 2.7 weight percent diethylene glycol mono n-butyl ether (DB) and 0.2 weight percent triethylene glycol mono n-butyl ether (TB). The ratio of the mono adduct EB to highers (DB, TB and poly adducts) was 10.0:1.0.

EXAMPLE 5

$Fe^{2+}$ form Dowex® MSC-1 Catalyst

The reaction of Example 4 was carried out, but using the catalyst of Example 2 and a temperature of 80° C. The reactor yielded a product containing 24.1 weight percent EB, 2.1 weight percent DB and 0.2 weight percent TB. The ratio of mono adduct EB to highers was 10.5:1.0.

EXAMPLE 6

KOH Catalyst (Not of the Invention)

The reaction of Example 4 was carried out but with 0.02 g KOH per 100 g feed as the catalyst and at 190° C. for 3 hours. The reaction yielded a product containing 20.3 weight percent EB, 7.6 weight percent DB and 2.2 weight percent TB. The ratio of the mono adduct EB to highers was 2.1:1.0.

EXAMPLES 7–28

Additional examples are contained for ease of comparison in the following Table I. These examples were all conducted utilizing as reactors a ⅜" stainless steel tube with end caps. The volume of these tubes were 7 ml each. The indicated catalyst, Compound A (hydroxyl containing) and Compound B (oxirane containing) were placed in a cooled (about −20° C.) reactor and the tubes sealed. The reactors were then placed in a temperature controlled environment (temperature as indicated) and mildly agitated with a rocking motion. After reaction at the desired temperature for the desired time, the reactors were cooled in an ice/water bath for ten minutes. Then the reactors were opened and the contents analyzed by standard gas chromatography procedures using a Hewlett-Packard® 5700A gas chromatograph equipped with a ⅛"×10' glass column packed with 15 percent Triton-X® 305 on Chromsorb® W/HP and using a thermal conductivity detector.

The product mixture concentrations listed designate the weight percentage of total product eluted from a gas chromatography column. Any nonvolatile (i.e., higher boiling than pentaethylene glycol) products would not elute from the gas chromatography column and are therefore unaccounted. An approximate indication of the level of nonvolatile components can be obtained by an oxide balance between the feed and the product. Compounds A and B listed under Product Mixture Concentrations are unreacted amounts of the reactants. The mono-adduct is the most desired product. "Other" highers include the tri- through penta-adducts. "Glycols" include the mono- through penta-adducts. By summing the product mixture concentrations listed and subtracting from 100, one may obtain the weight percentage of undesirable reaction products which include dioxanes, aldehydes and polymer products.

The weight percentages of the catalysts are based on the combined weights of Compound A and Compound B. The temperature (T) is given in degrees centigrade and the time of reaction (t) in hours (hr).

TABLE I

| # | Catalyst (C) | Wt % C | Reactants A | Reactants B | A:B Wt Ratio | T (°C.) | t (hr) | B | A | Mono Adduct | Higher Adducts Di- | Higher Adducts Other | Glycols |
|---|---|---|---|---|---|---|---|---|---|---|---|---|---|
| 7 | $Mg^{++}$/Dowex® MSC-1 | 10.0 | n-butanol | EO | 21:4 | 120 | 3.0 | 0.39 | 67.3 | 23.2 | 1.60 | 0.22 | 2.00 |
| 8 | $Mg^{++}$/Dowex® MSC-1 | 10.0 | n-butanol | EO | 21:4 | 120 | 3.0 | 0.61 | 70.0 | 24.0 | 1.84 | 0.50 | 1.88 |
| 9 | $Mg^{++}$/Dowex® MSC-1 | 2.5 | ethanol | EO | 19:6 | 120 | 3.0 | 6.51 | 58.8 | 29.3 | 2.43 | 0.27 | 1.27 |
| 10 | $Mg^{++}$/Amberlyst® 15 | 23.0 | n-butanol | EO | 17:3 | 100 | 3.0 | 5.8 | 73.8 | 14.4 | 2.73 | 0.96 | 2.38 |
| 11 | $Mg^{++}$/Nafion® | 23.0 | n-butanol | EO | 17:3 | 100 | 3.0 | 7.3 | 69.3 | 21.6 | 1.09 | — | 0.09 |
| 12 | $Fe^{++}$/Dowex® MSC-1 | 23.0 | n-butanol | EO | 21:4 | 100 | 3.0 | — | 77.1 | 11.4 | 0.56 | 0.65 | 4.15 |
| 13 | $Ca^{++}$/Dowex® MSC-1 | 10.0 | n-butanol | EO | 21:4 | 120 | 3.0 | 0.04 | 68.8 | 22.4 | 0.50 | 0.48 | 6.48 |
| 14 | $Sr^{++}$/Dowex® MSC-1 | 5.0 | ethanol | EO | 3:1 | 120 | 3.3 | 0.48 | 58.91 | 33.19 | 4.12 | 0.80 | 1.26 |
| 15 | $Zn^{++}$/Dowex® MSC-1 | 5.0 | ethanol | EO | 3:1 | 120 | 3.3 | 0.05 | 57.17 | 30.96 | 2.16 | 1.27 | 1.34 |
| 16 | None | — | n-butanol | EO | 21:4 | 180 | 2.0 | 12.49 | 74.7 | 12.1 | 0.47 | — | 0.09 |
| 17 | None | — | ethanol | EO | 3:1 | 120 | 3.3 | 15.05 | 66.53 | 16.07 | 2.11 | 0.16 | 0.06 |
| 18 | $Na^+$/Dowex® MSC-1 | 5.0 | ethanol | EO | 3:1 | 120 | 3.3 | 12.12 | 62.78 | 18.69 | 3.07 | 0.01 | 0.13 |
| 19 | $H^+$/Dowex® MSC-1 | 1.0 | ethanol | EO | ∼13:7 | 120 | 3.0 | 20.00 | 59.7 | 13.3 | 1.47 | 0.71 | 0.11 |
| 20 | KOH | 0.05 | n-butanol | EO | 21:4 | 180 | 2.0 | 0.01 | 64.9 | 21.2 | 8.53 | 4.52 | 0.69 |
| 21 | KOH | 1.0 | ethanol | EO | ∼13:7 | 190 | 2.0 | 0.07 | 44.4 | 27.5 | 15.6 | 12.14 | 0.16 |
| 22 | KOH | 1.0 | ethanol | EO | ∼13:7 | 120 | 3.0 | 3.60 | 44.9 | 27.0 | 14.9 | 9.06 | 0.03 |
| 23 | $MgSO_4$ | 10.0 | n-butanol | EO | 21:4 | 120 | 3.0 | 4.83 | 70.4 | 21.5 | 1.67 | 0.15 | 1.07 |

TABLE I-continued

| # | Catalyst (C) | Wt % C | Reactants A | B | A:B Wt Ratio | T (°C.) | t (hr) | Product Mixture Concentrations | | | | | |
|---|---|---|---|---|---|---|---|---|---|---|---|---|---|
| | | | | | | | | B | A | Mono Adduct | Higher Adducts Di- | Other | Glycols |
| 24 | MgSO$_4$ | 4.0 | n-butanol | EO | 21:4 | 180 | 2.0 | 0.01 | 64.5 | 27.7 | 3.29 | 0.35 | 1.37 |
| 25 | MgSO$_4$ | 10.0 | n-butanol | EO | 21:4 | 180 | 2.0 | 0.01 | 62.2 | 28.3 | 3.66 | 0.54 | 1.68 |
| 26 | MgSO$_4$ | 0.8 | ethanol | EO | ~14:6 | 190 | 3.45 | 4.59 | 44.6 | 32.6 | 7.89 | 1.77 | 5.24 |
| 27 | CaSO$_4$ | 2.5 | ethanol | EO | 3:1 | 150 | 2.0 | 3.37 | 63.72 | 19.68 | 7.26 | 4.91 | 0.52 |
| 28 | ZnSO$_4$ | 2.5 | ethanol | EO | 3:1 | 150 | 2.0 | 2.06 | 53.2 | 33.86 | 6.15 | 0.93 | 2.74 |

Comparison of Example 1 exemplifying the process of the invention with Example 3 showing a process using a conventional catalyst reveals several advantages made available by the present invention over the prior art. In the reaction of ethylene oxide with ethanol, not only did the process of the invention yield more of the preferred product, viz. 39.9 weight percent using Mg++/Dowex ® MSC-1 versus 27.1 weight percent using KOH, but it did so at a lower temperature (102° C. versus 150° C.). The conventional catalyst is used in a homogeneous catalytic reaction while the catalyst of the present invention is substantially heterogeneous with the reaction product mixture, thereby eliminating or greatly reducing separation and purification costs. Also a ratio comparison of the mono-adduct to higher adducts on a weight basis gave a 7.8:1.0 ratio for the instant process versus 2.6:1.0 for the conventional process catalyzed by KOH.

Similarly, comparison of Example 2 of the invention with Example 3 presents a greater yield (32.4 versus 27.1 weight percent) at an even lower temperature (80° C. versus 150° C.). A higher selectivity toward the mono adduct is noted (10.8:1.0 versus 2.6:1.0). Comparison of Example 1 with Example 2 (both examples of the invention) show a greater yield for Example 1, but better mono selectivity for Example 3.

The above comparisons were repeated for the reaction of n-butanol with ethylene oxide using the same catalysts as in Examples 1, 2 and 3 with Examples 4 and 5 being of the instant invention and 6 being the conventional KOH catalyst. In comparing Example 4 with Example 6, the process of the invention yielded 29.0 weight percent versus 20.3 weight percent of the preferred product for the process using a conventional catalyst. The inventive process was carried out at a temperature substantially less than that typical of a process using a strong base catalyst and gave a (mono/-higher) adduct ratio of 10.0:1.0 versus 2.1:1.0 for the known process of Example 6. The heterogeneous nature of the inventive process yields lower separation and purification costs with this product mixture also.

Comparison of Example 5 of the invention with Example 6 shows a yield of 24.1 versus 20.3 weight percent of EB but at an even lower temperature of 80° C. and with a selectivity ratio of 10.5:1.0 compared to 2.1:1.0 for the KOH catalyzed process.

Table I contains additional Examples 7 through 28 with Examples 7-15 being of the invention and Examples 16-28 included for comparison purposes. Note that comparison of the noncatalyzed process in Runs 16 and 17 produced a relatively good product mixture with high selectivity toward the preferred mono product, however, the conversion rate was in each case much lower than that of the instant invention. Also Run 16 which had the highest selectivity was conducted at a temperature at least 60° C. hotter than Runs 7-15 of the invention.

In a comparison of the H+ form of a sulfonated styrene divinylbenzene copolymer resin of Run 19 with Runs 7-15 of the invention, it is seen that at equivalent temperatures the instant invention produces from 9.1 to 19.89 weight percent more of the preferred product. Runs 7-15 have mono/highers ratios ranging from 4.2:1.0 for Run 10 to 22.9:1.0 for Run 13 while the H+ form (not of this invention), (Run 19) has a ratio of 6.1:1. Also the H+ form catalyst tends to be high in by-product formation.

The alkali metal exchanged sulfonated divinylbenzene/styrene copolymer comparative example in Run 18 gave substantially the same results as uncatalyzed Run 17. Although the yield of the mono adduct increased slightly so did the di-adduct and also by-products.

Examples 20 through 22 underscore the propensity of KOH catalyzed processes to the formation of higher adducts. Note too that Examples 7-28 were all conducted as batch reactions.

Examples 23 through 28 are comparative examples of alkaline earth sulfates. These catalysts have sufficient solubilities in the reaction product mixtures to necessitate costly separation and purification steps that are either unnecessary or ameliorated by the process of the invention. Furthermore, the ratio of mono/highers for Runs 23-48 ranges from 1.6 to 11.8 indicating that the instant invention typically is more selective toward the mono adduct product. Impurity formation has also been noted as a problem with these catalysts.

Further modifications of the invention disclosed will be apparent to those skilled in the art and all such modifications are deemed to be within the scope of the invention as defined by the following claims.

What is claimed is:

1. A process comprising reacting an organic compound (A) having at least one aliphatic hydroxyl group with an oxirane compound (B) under reaction conditions to form a glycol ether, said process occurring in the presence of a catalytic amount of a polymeric material that is substantially insoluble in the reaction mixture, said polymeric material being selected from the group consisting of sulfonated styrene-divinylbenzene copolymers, sulfonated polyethylene resins, and perfluorosulfonic acid polymers having a plurality of pendant sulfonate moieties with divalent metal counterions selected from the group of 2a, 2b and 8 elements of the Periodic Table.

2. A process as defined in claim 1 wherein said Compound A is a monohydric aliphatic alcohol.

3. A process as defined in claim 1 wherein said Compound B contains a terminal oxirane group.

4. A process as defined in claim 1 wherein said Compound B is ethylene oxide.

5. A process as defined in claim 1 wherein said divalent metal counterions are alkaline earth metal cations.

6. A process as defined in claim 5 wherein said alkaline earth metal cation is magnesium.

7. A process as defined in claim 5 wherein more than one type of metallic counterion is present.

8. A process as defined in claim 1 wherein said glycol ethers are of the formula

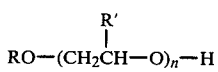

wherein R is an organic group; R' is H or an organic group and n is a positive integer.

9. A process as defined in claim 8 wherein a ratio of the adduct $n=1$ to the adducts $n>1$ is at least about 3:1.

10. A process as defined in claim 1 wherein said reaction conditions comprise reacting under autogenous pressure at a temperature in the range of about 80° C. to about 120° C.

11. A process as defined in claim 10 wherein said reaction conditions further comprise a reaction time in the range of about 0.5 to about 2.0 hours.

12. A process as defined in claim 11 wherein said Compound A and Compound B are introduced in a molar ratio range of about 8:1 to about 1:1.

13. A process as defined in claim 11 wherein said polymeric material is present in the range of about 5 to about 50 percent by weight based on the total combined weight of said Compound A and Compound B.

14. A process as defined in claim 1, 4, 9, 11 or 14 wherein said polymeric material is a styrene-divinylbenzene copolymer resin.

15. A process as defined in claim 1 or 10 wherein said polymeric material is Nafion.

16. A process as defined in claim 14 wherein said Compound A is methanol, ethanol or n-butanol.

17. A process as defined in claim 16 wherein said resin is Dowex ® MSC-1.

18. A process as defined in claim 1 or 13 wherein said divalent metal counterion is iron.

19. A process as defined in claim 13 wherein said polymeric material is essentially insoluble and the divalent metal counterion is magnesium or iron.

* * * * *